United States Patent [19]
Tuchler

[11] Patent Number: 5,119,821
[45] Date of Patent: Jun. 9, 1992

[54] DIVERGING SIGNAL TANDEM DOPPLER PROBE

[76] Inventor: Robert E. Tuchler, 176 Seeley St. #8A, Brooklyn, N.Y. 11218

[21] Appl. No.: 473,569

[22] Filed: Feb. 1, 1990

[51] Int. Cl.[5] ............................................. A61B 8/06
[52] U.S. Cl. ........................ 128/664.04; 128/662.05; 128/662.06
[58] Field of Search ...................... 128/662.03–662.06; 73/861.25

[56] References Cited

U.S. PATENT DOCUMENTS

| | | | |
|---|---|---|---|
| 3,631,849 | 1/1972 | Norris | 128/66 |
| 3,766,517 | 10/1973 | Fahrbach | 73/861.25 |
| 3,780,725 | 12/1973 | Goldberg | 128/662.04 |
| 3,940,731 | 2/1976 | Cooper et al. | 73/861.25 |
| 3,987,673 | 10/1976 | Hansen | 73/861.25 |
| 4,097,835 | 6/1978 | Green | 367/94 |
| 4,237,729 | 12/1980 | McLeod et al. | 128/662.06 |
| 4,259,870 | 4/1981 | McLeod et al. | 73/861.25 |
| 4,407,293 | 10/1983 | Suarez, Jr. et al. | 128/661.09 |
| 4,413,629 | 11/1983 | Durley, III | 128/662.03 |
| 4,459,854 | 7/1984 | Richardson et al. | 128/662.03 |
| 4,492,120 | 1/1985 | Lewis et al. | 73/625 |
| 4,541,433 | 9/1985 | Baudino | 128/662.06 |
| 4,605,009 | 8/1986 | Pourcelot et al. | 128/662.06 |
| 4,674,336 | 6/1987 | Johnston | 73/861.25 |
| 4,722,347 | 2/1988 | Abrams et al. | 128/662.06 |
| 4,757,821 | 7/1988 | Snyder | 128/662.06 |
| 4,869,260 | 9/1989 | Young et al. | 128/662.06 |
| 4,947,954 | 8/1990 | Rabinovitz et al. | 128/662.06 |

FOREIGN PATENT DOCUMENTS 3714747 11/1988 Fed. Rep. of Germany ........................ 128/662.06

OTHER PUBLICATIONS

Born, N. et al, "Early and Recent Intra-Luminal Ultrasound Devices", Intnl Jrnl of Caridac Imaging, v. 4:79–88, 1989.

Primary Examiner—Francis Jaworski
Attorney, Agent, or Firm—Blum Kaplan

[57] ABSTRACT

A dual transducer probe for measuring blood flow by Doppler effect measurement in which quantitative flow data can be compiled and flow constriction points as small as 10% and less can be pinpointed with relative ease. The probe is formed with two transducers, oriented at about 45° from a bottom contacting surface of the probe so that transmission signals diverge at an angle of about 90°. A first transducer directs pulsed sound waves into the direction of blood flow and a second transducer directs pulsed sound waves with the direction of blood flow. The transducers act as receivers for the respective pulses. Fluid velocity can be calculated due to the Doppler effect. By analyzing the signal frequency shifts from the two transistors the blood flow at a very minute region between the transducers, can be determined. Constrictions, corresponding to changes in flow can be pinpointed by moving the probe along the blood vessel.

24 Claims, 7 Drawing Sheets

DIVERGING SIGNAL TANDEM DOPPLER PROBE

BACKGROUND OF THE INVENTION

The invention relates generally to a probe for measuring fluid flow and more particularly to a dual transducer probe for measuring fluid flow by employing diverging ultrasound signals according to the Doppler effect principle, especially through blood vessels.

In the field of medical practice, it is often desirable to obtain data regarding blood flow within an individual's blood vessels such as the arteries, veins and capillaries to assist in medical diagnosis, prognosis and treatment. Early microsurgeons appreciated the need for reliable and accurate direct evidence of anastomotic patency such as flap coloration, capillary refill, or peripheral bleeding. Often, surgeons had to rely on a subjective assessment of various types of pulsations postanastomotically.

A dual forceps or "milking" procedure was proposed by J. W. Hayhurst, et al. in "An experimental study of microvascular technique, patency rates and related factors.", Br. J. Plast Surg 28:128-32 (1975). However, this method is disadvantageous due to its traumatic nature and occurrences of proven thrombotic reduction of the lumen by 75-95% in which the anastomoses were classified as fully patent.

An apparatus for measuring the speed of blood flowing through channels by the use of ultrasound according to the Doppler effect principle is described in U.S. Pat. No. 3,766,517 to Fahrbach, the contents of which are incorporated herein by reference. Fahrbach describes a probe having two transmitting/receiving transducers that project a converging signal in which the sending-receiving directions of the transducers form an angle of 90°.

Continuous Wave Doppler Ultrasound was described as being useful to assess microvascular anastomotic patency by Van Beek, et al. in "Ultrasound evaluation of microanastomosis", Arch Surg 100:945-949 (1975) Van Beek, et al. describe several velocity profile waveform parameters that they felt would be predictive or ultimate anastomotic patency, but made no substantial attempt to relate these criteria to quantitation of luminal narrowing.

Luminal narrowing was addressed by Freed, et al. in "High frequency pulsed Doppler ultrasound: a new tool for microvascular surgery", J.Microsurg 1:148-153 (1979), the contents of which are incorporated herein by reference. Freed, et al. applied High Frequency Pulse Doppler Ultrasound (HFPDU) to the field of microsurgery. Freed, et al. attempted to quantitate arterial stenoses ranging from 25-99% in vessels having a diameter less than 1 mm using a simple velocity ratio equation:

$$\% \text{ Area Reductions} = 100[1 - V_p/V_s]$$

wherein Vp and Vs represent pre-stenotic and stenotic velocities, respectively.

Figure 1:
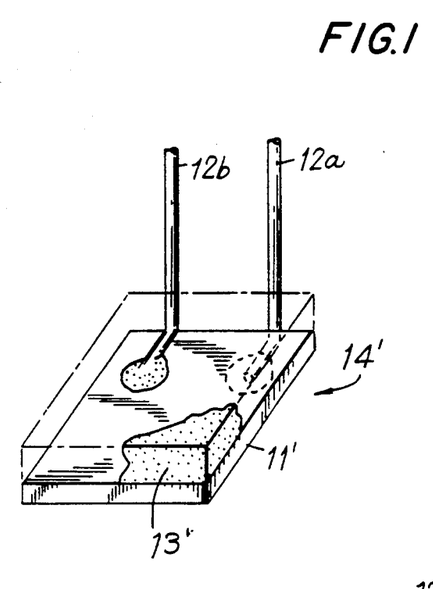
FIG. 1 is a perspective view of a transducer constructed in accordance with the invention.
Figure 2:
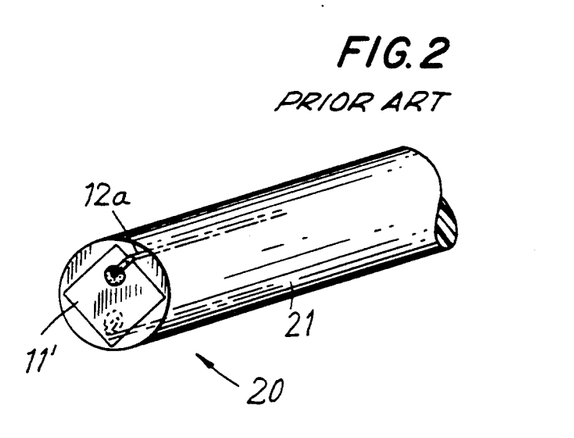
FIG. 2 is a perspective view of a prior art probe for measuring blood flow.

The Freed, et al. technique involves meticulous scanning of a microanastomosis at 0.5 mm intervals with a pencil-type probe. A needle-mounted pencil-type probe 20 shown in FIG. 2, including the piezoelectric-crystal transducer 14' shown in FIG. 1 is employed. Transducer 14' is formed of a 1 $mm^2$ piezoelectric crystal 11' electrically coupled to a pair of electric lead wires 12a and 12b. A styrofoam acoustic baffle 13' is disposed on an inner surface of crystal 11'.

Figure 3:
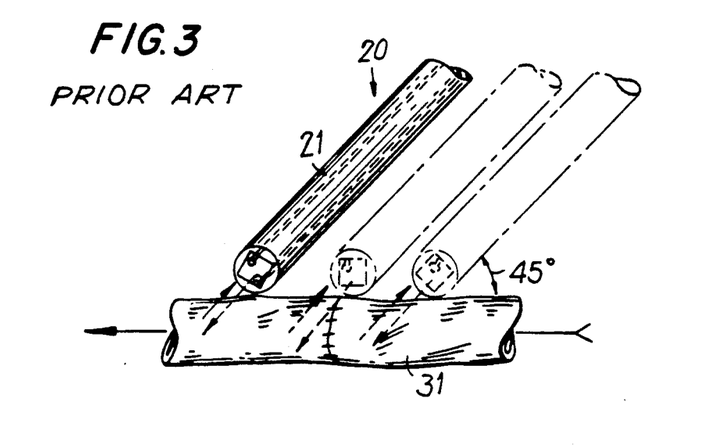
FIG. 3 is a perspective view showing the use of the probe shown in FIG. 2.

As shown in FIG. 3, transducer 14 is mounted flush to the end of a twenty gauge needle 21 and is positioned at an angle of 45° to a blood vessel 31 by hand or with a micromanipulator. Transducer 14 is sequentially scanned across the microanastomosis. This technique has been found to be impractical in a clinical setting.

Conventional Doppler effect fluid flow measuring probes have disadvantages. While the probes can be effective for determining whether fluid is flowing through a vessel in some clinical settings, they can be inappropriate for determining quantitative fluid flow values or for pinpointing constricted areas. Thus, conventional probes are not fully satisfactory and have inadequacies due to their shortcomings.

Accordingly, it is desirable to provide an improved fluid flow probe which avoids the shortcomings of the prior art.

SUMMARY OF THE INVENTION

Generally speaking, in accordance with the invention, a dual transducer probe for measuring blood flow by Doppler effect measurement is provided in which quantitative flow data can be compiled and fluid flow constriction points can be pinpointed with relative ease. The probe is formed with two transducers, oriented at preferably about 45° from a bottom contacting surface of the probe so that transmission signals diverge at an angle of preferably about 90°. A first transducer directs pulsed sound waves into the direction of blood flow and a second transducer directs pulsed sound waves with the direction of blood flow. The transducers act as receivers for their respective pulses. Fluid velocity can be calculated because of the Doppler effect. By analyzing the signal frequency shifts from the two transducers, the blood flow at a very minute cross section of the blood vessel between the transducers can be determined. Constrictions as small as 10% and below, corresponding to changes in flow, can be pinpointed by moving the probe along the blood vessel.

Accordingly, it is an object of the invention to provide an improved probe for measuring fluid flow.

Another object of the invention is to provide an improved probe and method for pinpointing minute perturbations in flow constrictions or faulty repairs in blood vessels.

A further object of the invention is to provide an improved probe and method for determining flow patterns through blood vessels having small diameters.

Still another object of the invention is to provide an improved probe for measuring flow through blood vessels which is easy and convenient to use.

Still a further object of the invention is to provide a probe to study end to end repairs as well as end to side repairs of any angle.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

A tandem doppler probe (TDP) for measuring fluid flow in accordance with the invention is constructed with two sound transmitting/receiving sources positioned to transmit the sound signals at a diverging angle into the flowing fluid. A particularly well suited tandem doppler probe 40 constructed in accordance with the invention is shown generally in FIGS. 4 and 5. Probe 40 includes a pair of transducers 41a and 41b, each oriented at an angle F to a bottom surface 42 of probe 40. Angle F is preferably about 45° but other angles are also suitable. Bottom surface 42 is adapted to be placed in contact with a blood vessel 43 that can have a diameter as small as about 1 mm or less. Probe 40 can be formed with a pair of guide ridges 46a and 46b to assist in aligning probe 40 with blood vessel 43 so that transducers 41a and 41b can be conveniently aligned with the direction of blood flow.

Figure 4:
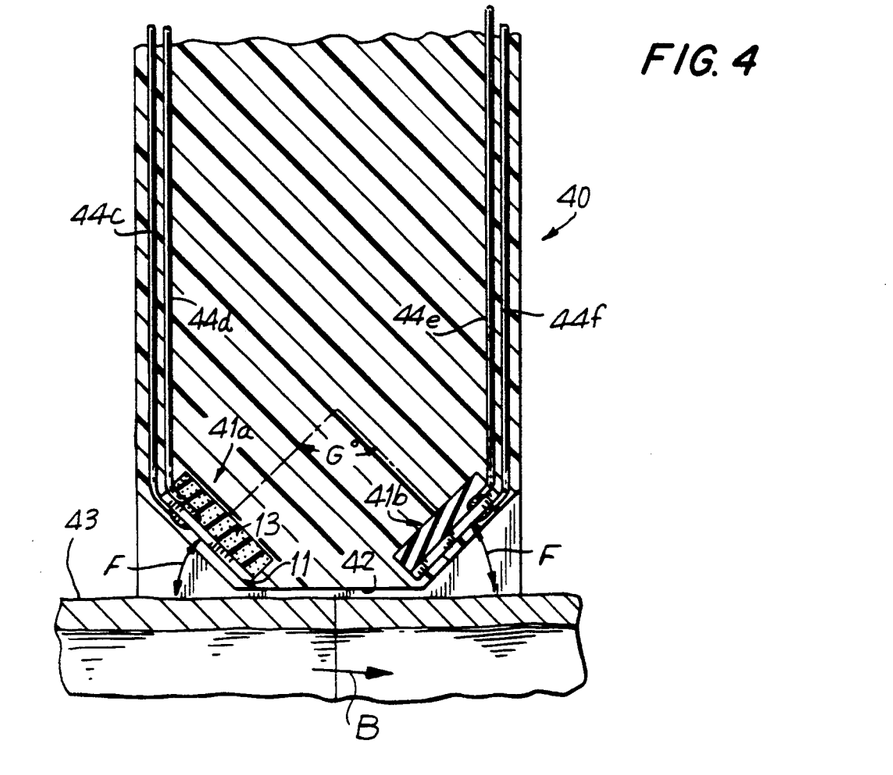
FIG. 4 is a cross sectional view of a probe constructed in accordance with the invention positioned for measuring fluid flow through an artery.
Figure 5:
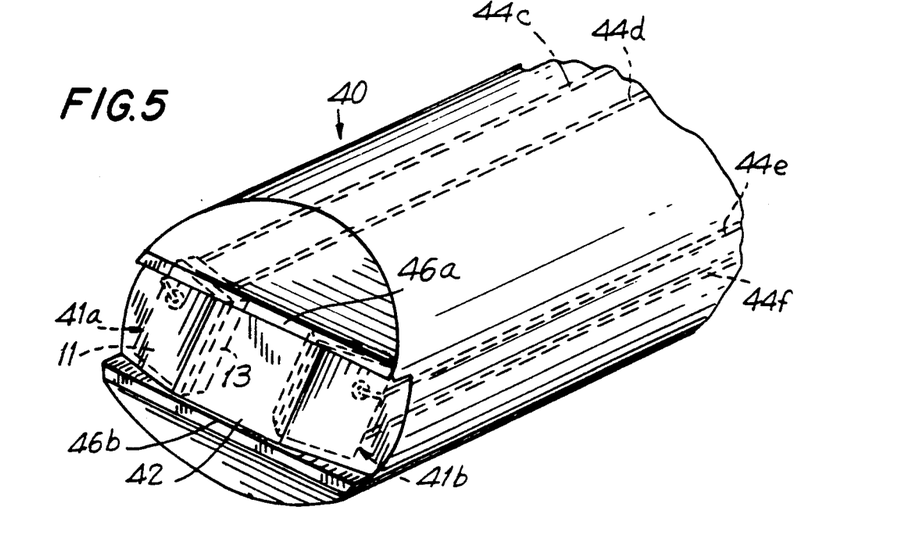
FIG. 5 is a perspective view of a probe constructed in accordance with the invention.

Bottom surface 42 may also be configured differently so the bottom edges of transducers 41a and 41b which are perpendicular to guide ridges 46a and 46b are not parallel, to study flow through branched vessels or repairs done in "end to side" fashion. In this configuration, guide ridges 46a and 46b would be bent at an angle and transducers 41a and 41b would be aligned with the bent ridges to match the configuration of a forked or curved blood vessel.

Referring to FIG. 4, blood flows in the direction of an arrow B. Transducers 41a and 41b are oriented to transmit signals diverging at an angle G. Angle G is preferably 90°, but other angles are also suitable. The absolute angle of each transducer is not as critical as the relative angle between transducers 41a and 41b.

Transducer 41b transmits a pulsed signal in the direction with fluid flow and receives the delayed returning signal. Transducer 41a transmits a pulsed signal into the direction of fluid flow and receives the signal of increased frequency. The delay and increase in signal frequency is caused by the Doppler effect. By analyzing the difference in the frequency between transmission and reception by conventionally known methods, the blood flow across the cross section of the blood vessel at the minute region between the transducers can be measured Constrictions corresponding to changes in flow can be detected by moving the probe along the vessel. The device can be positioned so that one transducer reads the flow proximally and the other distal to or at an anastomosis to provide two doppler tracings simultaneously for instant comparison of blood flow on either side of an anastomosis or stenosis.

The electronics for a tandem Doppler probe (TDP) such as probe 40 are commonly known and are similar to the electronics discussed in the Freed article, J. Microsurgery 1: 148-153 (1979) and in several U.S. patents such as U.S. Pat. No. 3,987,673 to Hansen, the contents of which are incorporated herein by reference. Additional information can be obtained from the Cardiovascular Sciences Laboratory of the Baylor College of Medicine and other publically accessible sources.

High Frequency Pulsed Doppler Ultrasound (HFPDU) is particularly well suited for measuring blood flow with a tandem doppler probe constructed in accordance with the invention. The pulsed technique provides advantages for the study of blood flow in vessels within a microsurgical domain. The elimination of separate transmitting and receiving crystals in the probe head reduces the bulk of the probe head in half and eliminates the acoustic window dead-space directly in front of the crystals. This construction permits placement of the crystal directly on the probe wall.

Acoustic scattering is proportional to the fourth power of the frequency. Accordingly, the increase in frequency to 20MHz permits the use of piezoelectric crystals that are as small as about 0.5 mm squares. By addition of the variable delay time between transmission and reception of ultrasonic pulses, a discrete sample of volume of less than a cubic millimeter can be placed anywhere between about 0.5 and 10 mm from the probe face. This high spatial resolution permits generation of complex, parabolic velocity profiles by sampling across the lumen of a vessel in increments as small as about 0.1 mm. The compact probe face allow a meniscus of saline to act as an acoustic coupling agent obviating the need for gels or creams.

HFPDU can be employed to create precise cross-sectional velocity profiles in a study of the hemodynamic characteristics of normal anastomoses and the effect of topical lidocaine on vasospasm as described in Blair, "Hemodynamics after microsurgical anastomoses: the effects of topical lidocaine.", J. Microsurg, 2:157-164 (1981), the contents of which are incorporated herein by reference.

Lee, et al. used this modality successfully to compare the waveforms traversing microsurgical vein graphs inserted with either continuous or interrupted suture technique in "Effect of suture technique on blood velocity waveforms in the microvascular anastomoses of autogenous vein graph", Microsurgery, 4:151-156 (1983).

To construct a preferred version of tandem doppler probe 40, transducers 41a and 41b are first constructed. A 20MHz gold-plated piezoelectric-crystal such as those available from the Valpey-Fisher Company is formed into 1.0 mm squares such as by using a steel rule and Carbide scribe under an operating microscope to yield a crystal 11. Other sizes for crystal 11 are also acceptable Crystal 11 is soldered to lengths of wire, such as silver wire which can be obtained from braided EKG wire to yield four wire leads 44c, 44d, 44e and 44f. Crystal 11 is then coated with laminating epoxy such as Fibre-Glast, #88/87 to strengthen and insulate the joints.

It is preferable to degas the epoxy for approximately 30 minutes in a vacuum of at least 28 inches of mercury to remove dissolved gases which can form minute bubbles when the epoxy cures. The bubbles cause acoustic voids in the probe face which can significantly degrade the ultrasound signal. A 1 mm square block of styrofoam 13 can be disposed on a backside of crystal 11 to serve as an acoustic baffle and minimize stray ultrasound.

Transducers 41a and 41b are carefully melted into the surface of a 2×3 cm piece of Dental Modeling Wax such as by a brief application of the tip of a hot soldering pencil to the wax. A small metal shim cut at 45° can serve as a template for the probe face angle. Transducers 41a and 41b should be separated by distance of about 1 to 5 mm and preferably about 2.5 mm. The absolute angle of each transducer 41a and 41b is less significant than their relative position to one another, which is important.

Grooves 46a and 46b are carved alongside the crystals to provide ridges for facilitating probe positioning. A suitable probe-head mold is placed over transducers 41a and 41b and melted in place such as by using the tip of a soldering pencil.

A probe handle can be fashioned from a 2 cm long plastic cylinder similar to that of a 3 cc syringe barrel or from a disposable electronic thermometer sheath (IVAC). It is preferable to attach leads 44c–44f with the delicate joints of the crystals already permanently encased in the probe head at the appropriate angles. The head and body of the probe can be formed of solid epoxy. If the epoxy forming the head is not degassed, the resulting minute bubbles act as an effective ultrasound attenuator. This permits the elimination of styrofoam piece 13 from the construction.

The head is easily removed from the mold after it cures. Two pairs of insulated copper wire leads are soldered to silver leads 44c–44f and heat-shrink tubing can be applied to the closely-packed connections. The resulting unit is placed into a longer secondary mold which can be fashioned from an entire 3 cc syringe barrel or thermometer probe sheath which has had the closed end removed. The remainder of the mold can be filled with degassed epoxy and cured.

After removal from the second mold, the wax is carefully melted from the face of probe 40 which can then be ground to its final appearance with a high speed grinding wheel.

Probe 40 is suitable for use with an operating microscope, a dual channel oscilloscope and chart recorder and a multichannel HFPDU unit such as the Model VF-1 available from Crystal Biotech, Inc., New Englander Industrial Park, Kuniholm Dr., Holliston, MA 01746. This unit includes a "Doppler Master" which controls synchronization of up to 6 separate flow-channel modules for simultaneous, independent operation. The probe is attached to two flow channels and the polarities are selected to provide dual positive deflections on the oscilloscope or chart recorder. Probe 40 can be either hand-held or placed in an articulated arm.

Use of the tandem doppler probe constructed as described above in accordance with the invention in connection with the above described set-up will now be explained with reference to the following examples. These examples are presented for purposes of illustration only and are not intended to be construed in a limiting sense.

EXAMPLE 1

20 Sprague-Dawley rats (250–400 grams) were anesthetized with intraperitoneal Chloral Hydrate (4%) and their femoral vasculature was exposed via a longitudinal incision. Femoral arteries having a diameter of 0.8 to 1.3 cm were dissected atraumatically from the inguinal ligament to the origin of the Superficial Epigastric Vessels. Arteries were bathed in a small amount of Ringers Lactate or Normal Saline, which acts as an acoustic coupling agent and the probe was carefully placed on the artery. The range control of each channel was independently adjusted to obtain maximum centerline velocities as assessed by simultaneous oscilloscope comparison. The probes provided clear and consistent signals with only minimal manipulation.

Optimal recordings were obtained with the probe just barely touching or less than 1 mm away from the vessel wall with a meniscus of saline bridging the interface. Wider separation impairs the signal quality and adds significant background noise due to artifact from the random motion of the saline caused by arterial wall motion.

EXAMPLE 2

Several trials were performed in which the TDP measured a variety of graded stenoses as well as gradual noose occlusion using 10-0 nylon suture material. The stenoses were quantified by measurement of external luminal diameters with a microcaliper under high-power magnification (20×).

Figure 6:
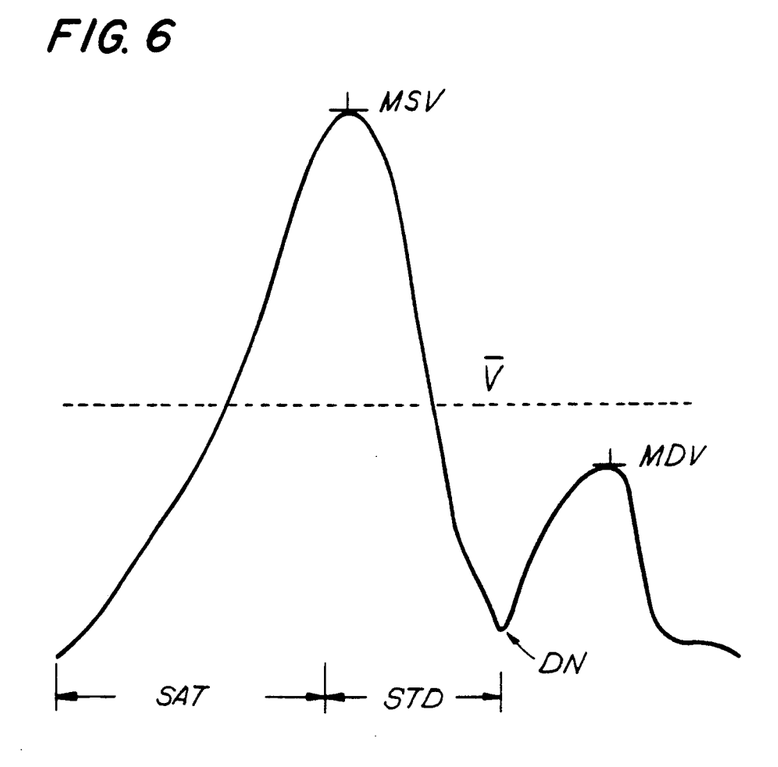
FIG. 6 is a schematic illustration showing an idealized HFPDU waveform.
Figure 7:
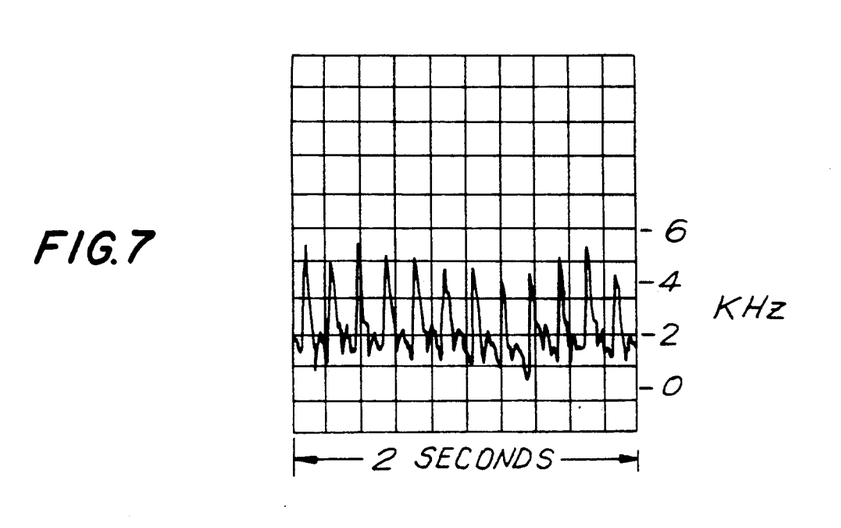
FIG. 7 is a graph showing actual HFPDU waveforms from a rat femoral artery over a two second interval.

As shown in FIGS. 6 and 7, the typical peripheral HFPDU waveform obtained from the rat shows a large initial systolic component followed by a smaller but positive diastolic deflection. An increase in velocity occurs during systolic acceleration time (SAT) until the maximum systolic velocity (MSV) is reached. Velocity decreases during systolic deceleration time (SDT) to the point at which the dichrotic notch (DN) is observed and then increases until the maximum diastolic velocity (MDV) is reached. V stands for the mean velocity. These animals demonstrate a Dichrotic notch in contrast to the negative deflection, representing a short period of flow reversal in early diastole seen in the classic Triphasic waveforms of larger animals and humans.

EXAMPLE 3

Figure 8:
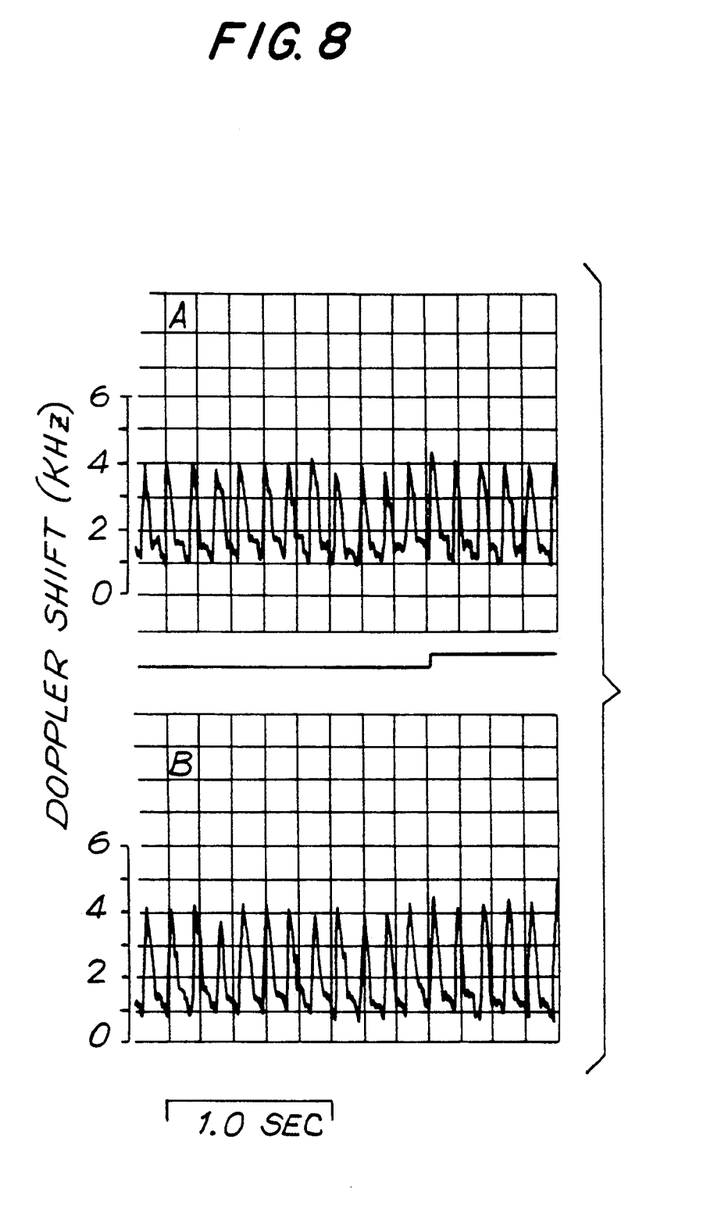
FIG. 8 is two graphs showing simultaneous HFPDU waveforms from a probe constructed in accordance with the invention to illustrate Doppler shift.
Figure 9:
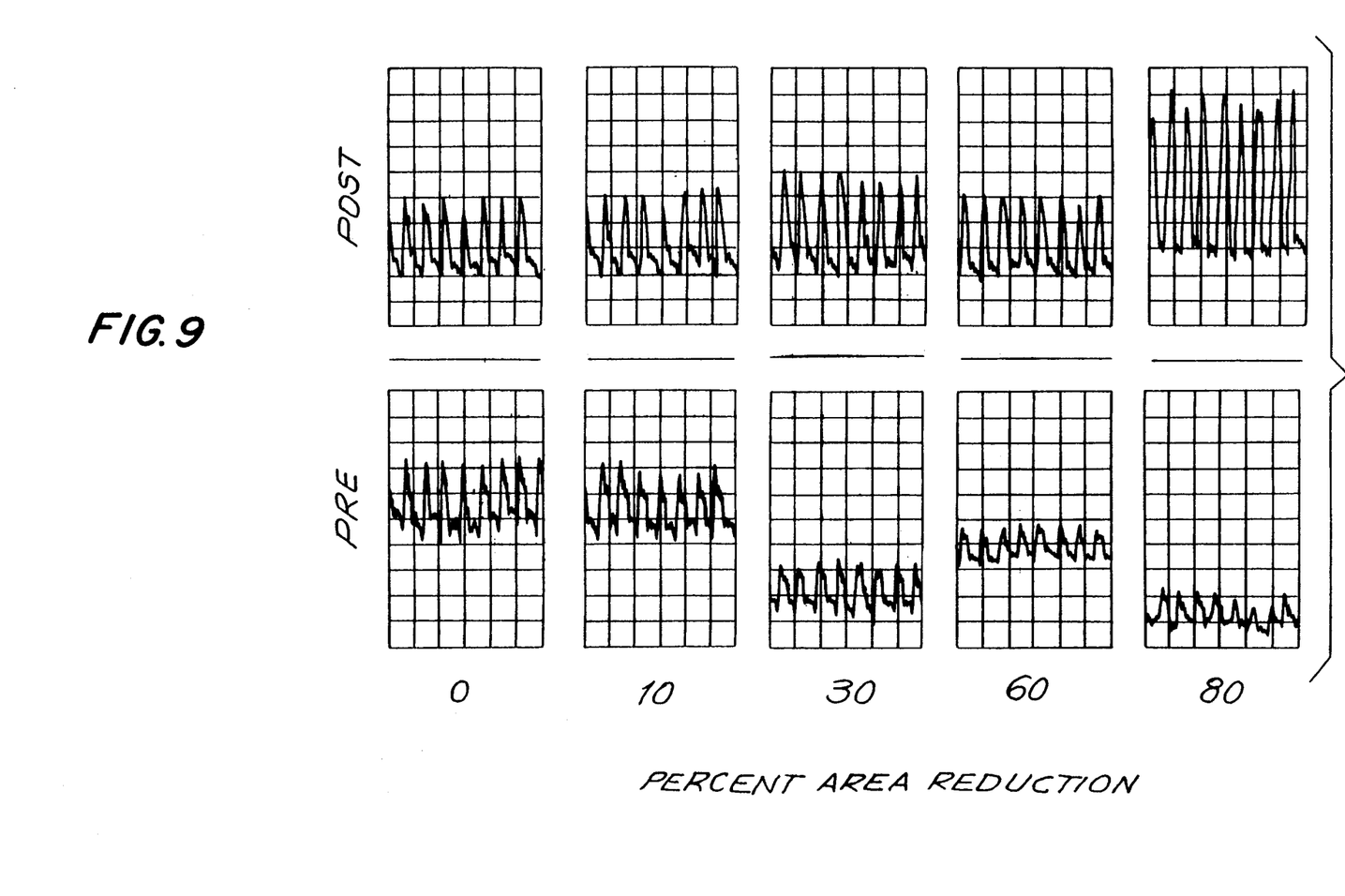
FIG. 9 is graphs showing HFPDU waveforms from a probe constructed in accordance with the invention to illustrate detection of flow constriction.

FIG. 8 shows waveforms obtained by placing the TDP on a segment of normal artery without a stenosis. Two sets of strips were produced and were identical except for being out of phase by an amount equal to the inter-crystal distance of the probe. The TDP was placed with one crystal in a pre-anastomotic position and the other face on or slightly distal to the stenoses. When adjusted to display maximum velocities, the probe clearly demonstrates graded stenoses as small as a 10% reduction in external vessel diameter, as shown in FIG. 9.

EXAMPLE 4

Figure 10:
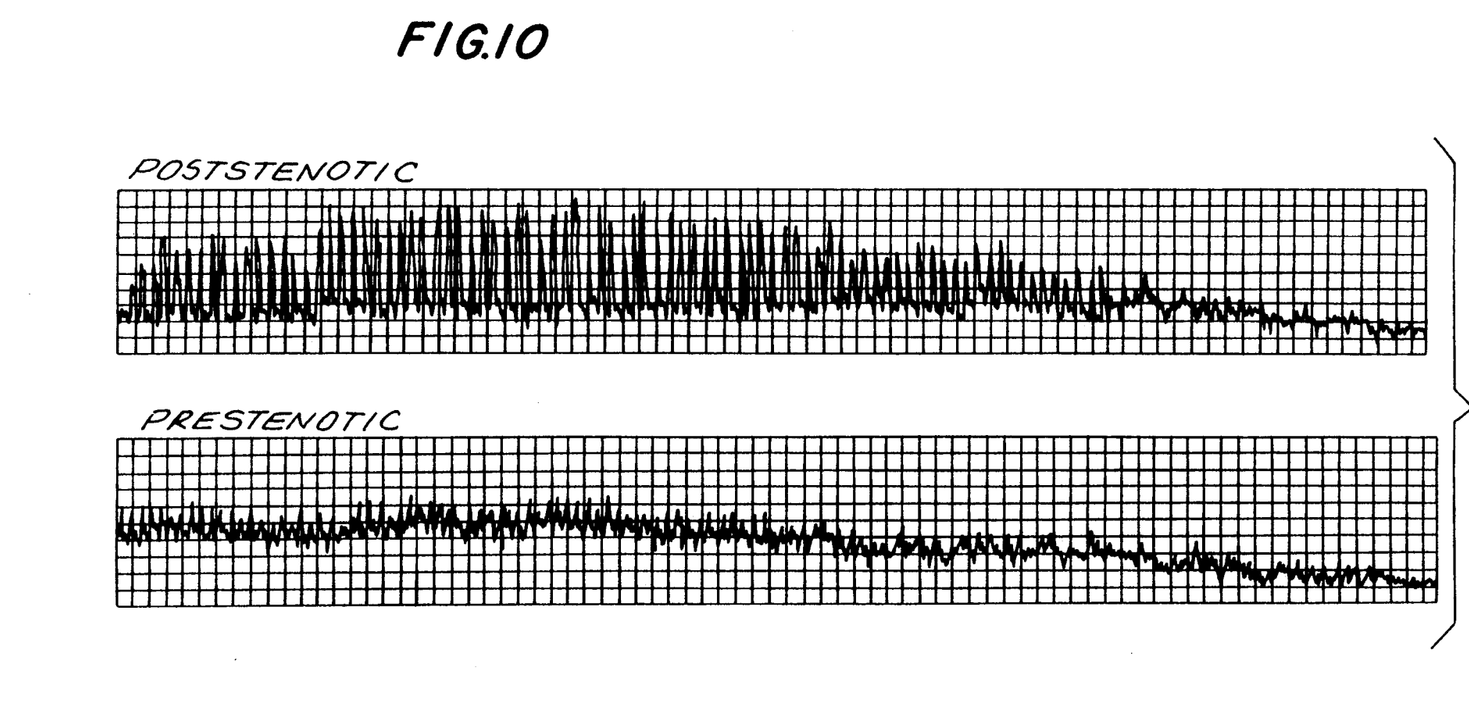
FIG. 10 is graphs showing HFPDU waveforms from a probe constructed in accordance with the invention to illustrate gradual noose occlusion of a 1.0 mm artery.

FIG. 10 shows waveforms produced by the TDP that result from gradual noose occlusion of a 1.0 mm artery. The post-stenotic crystal shows a linear increase in the maximum and mean velocities until approximately 50% reduction in cross-sectional area. At this point, values from both faces progressively decrease until the signal is lost, which occurs at complete occlusion.

EXAMPLE 5

Figure 11:
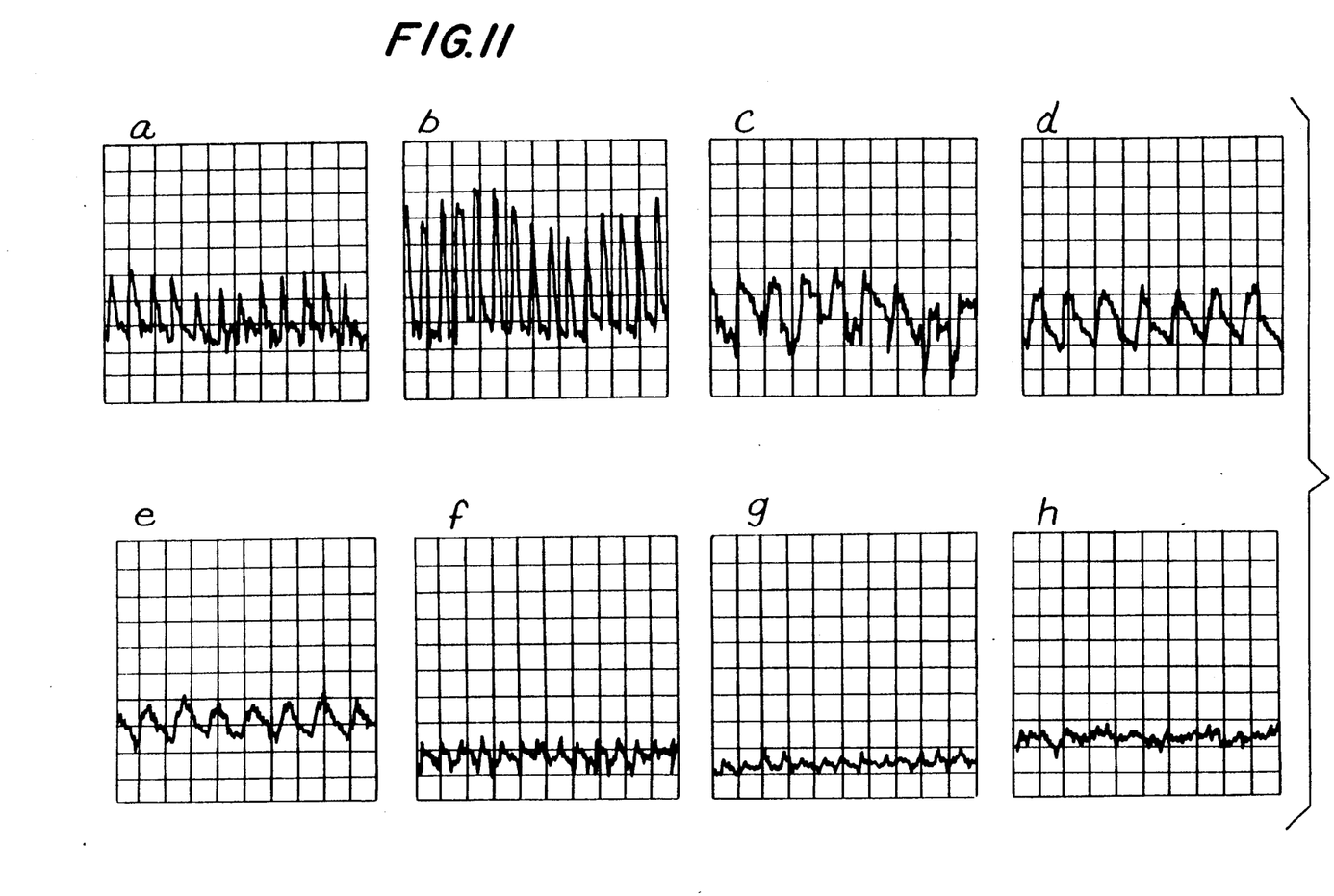
FIG. 11 is graphs showing HFPDU waveforms from a probe constructed in accordance with the invention to illustrate progressive arterial stenosis.

FIG. 11 shows characteristic changes in individual waveform morphology that is seen in progressive arterial stenoses which include: initial increase followed by decrease in maximum and mean velocities, slowed systolic acceleration time, loss of diastolic component and dichrotic notch and progressive rounding and attenuation of the terminal signal component until loss.

TABLE 1

Characteristic post-stenotic waveform morphology obtained with progressive occlusion as shown in FIG. 11.

| Chart letter | Morphology |
| --- | --- |
| a | normal baseline |
| b | post-stenotic "jet" |
| c | region of turbulence with flow reversal |
| d, e, f, g | gradual blunting of waveform; slowing of acceleration/deceleration times; loss of diastolic component and dichrotic notch |
| h | residual background signal of complete occlusion |

The Tandem Doppler probe (TDP) constructed in accordance with the invention provides many advantageous features. The two probe faces are accurately and permanently related to one another so that only one set-up and reading are necessary. This saves time and reduces sampling error. Because data represent a ratio of two simultaneous readings, absolute values are de-emphasized and variations in systemic conditions such as arterial pressure, heart rate and peripheral resistance will not affect the results. In addition, because the TDP compares identical pulses at different locations, beat to beat variability is eliminated as a source of error. Due in part to these features and the fact that velocity and waveform changes occur both proximal and distal to the stenoses, the TDP can identify pathologies that could be missed or miscalculated by a single, post-stenotic monitor.

A TDP constructed in accordance with the invention permits accurate and quantitative determination of luminal narrowing as little as about 10%. It can provide the sensitivity necessary to perform detailed waveform analysis of various anastomotic catastrophes. It is expected that analysis of waveform "signatures" could be used to identify thrombosis, venous out flow obstruction, tortion, kinking, back-wall stitches, or extrinsic compression by sub-flap hematoma or fluid collection. Computer assisted flow analysis and spectral analysis of the microvasculature could add to the TDP's effectiveness.

The TDP provides a simple and accurate technique for examining flow in blood vessels of any size including those that can be smaller than 1 mm in diameter.

The TDP can simultaneously measure both pre and post-anastomotically without repositioning or manipulation. The two waveforms provided can be compared instantly to quantify anastomotic narrowing of as little as 10% and to appreciate subtle waveform changes that accompany anastomotic pathology. It is expected that the TDP will be able to detect narrowing as small as 5% and below. The TDP permits earlier and more precise delineation of anastomotic problems in the operating room and can provide an objective assessment of technique for the microsurgical trainee and may allow more sensitive post-operative monitoring of free tissue transfers in an implantable form.

A TDP constructed in accordance with the invention can serve as an ideal training device. It provides instant, atraumatic, hemodynamic assessment of "practice" anastomoses and provides objective feedback.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A probe for simultaneously measuring the flow of fluid flowing through a conduit on both sides of a specified cross-section of the conduit by employing the Doppler effect principle, comprising:

a housing having a bottom portion adapted for contacting a conduit;

a pair of transducer means on the housing, near the bottom portion, electrically coupled to electrical lead means, each transducer means adapted for independently receiving an electric signal from the lead means, converting the electric signal to a sound signal, and transmitting the sound signal towards a target in a fluid flowing through a conduit, so that the target will reflect the sound signal back to the same transducer means and each transducer means also adapted to convert the respective reflected sound signal to an electric output signal which is output from each transducer means via the lead means;

the pair of transducer means constructed and arranged to initially transmit the central portion of both sound signals in a diverging angle so that the central portion of one signal will be initially transmitted at an angle substantially opposite the overall direction of fluid flow and the central portion of the other signal will be initially transmitted at an angle substantially with the overall direction of fluid flow.

2. The probe of claim 1, wherein the sound signal is an ultrasound signal.

3. The probe of claim 1, wherein the sound signal is high frequency pulsed doppler ultrasound.

4. The probe of claim 3, wherein each transducer means includes a piezoelectric crystal having a flat side for facing towards the conduit and the crystals are positioned so that lines normal from one flat side will diverge from lines normal from the other flat side.

5. The probe of claim 1, wherein each transducer means includes a piezoelectric crystal having a flat side for facing towards the conduit and the crystals are positioned so that lines normal from one flat side will diverge from lines normal from the other flat side.

6. The probe of claim 5, wherein the flat side of the crystals are each oriented at about 45° to the bottom portion of the housing.

7. The probe of claim 6, wherein the bottom portion of the housing contains two pairs of parallel ridges, one pair for each transducer means, each pair oriented parallel with the direction of signal transmission from the respective transducer means, the ridges adapted for aligning the bottom portion with the configuration of a blood vessel.

8. The probe of claim 6, wherein the crystals are spaced less than about 5 mm apart.

9. The probe of claim 6, wherein one side of each crystal has an area of about 1 square millimeter.

10. The probe of claim 1, wherein the central portions of the transmitted signals diverge initially at an angle of about 90°.

11. The probe of claim 10, wherein each transducer means initially transmits the central portion of the signal at about 45° to the bottom portion of the housing.

12. The probe of claim 1 and including signal processing means responsive to the electric output signal from the transducers for determining the frequency shift due to the Doppler effect and provide separate displays from each transducer means.

13. A method of simultaneously measuring the velocity of blood flowing through a blood vessel on both sides of a specified cross section of the blood vessel, comprising:
reflecting a first ultrasound signal from the flowing blood by transmitting a first signal into the flowing blood from a position near to and on a first side of the cross section in the same direction with and at an angle to the flow of blood and determining the frequency shift of the first signal caused by the Doppler effect;
reflecting a second ultrasound signal from the flowing blood by transmitting the second ultrasound signal into the flowing blood from a position near to and on a second side of the cross section in an opposite direction to and at an angle to the flow of blood and determining the frequency shift of the second signal; and
comparing the frequency shift of the first signal to the frequency shift of the second signal.

14. The method of claim 13, wherein the first and second signals are initially transmitted at a diverging angle of about 90°.

15. The method of claim 13, wherein the first and second signals are transmitted at an angle of about 45° to the longitudinal axis of the blood vessel.

16. The method of claim 15, wherein the first and second signals are sent and received by respective piezoelectric crystal transducers mounted at the tip of a probe.

17. The method of claim 13, wherein the first and second signals are sent and received by first and second piezoelectric crystal transducers, respectively, mounted at the tip of a probe.

18. The method of claim 17, and including the step of displacing the probe tip along the blood vessel to determine positions of at least one of blood vessel constriction and repair inadequacies.

19. The method of claim 18, wherein constrictions as small as 10% can be detected.

20. The method of claim 17, wherein the blood vessel is less than about 1 mm in diameter.

21. The method of claim 17, wherein the blood vessel includes at least one of an anastomosis and a stenosis and the first and second crystals are positioned at or on either sides of the anastomosis or stenosis.

22. The method of claim 13, wherein the blood vessel includes at least one of an anastomosis and a stenosis and the first and second signals are transmitted to opposite sides of the anastomosis or stenosis.

23. A probe for simultaneously measuring the flow of fluid flowing through a conduit on both sides of a specified cross-section of the conduit, comprising:
a housing and a pair of transducers divergently oriented on the housing, each transducer adapted for independently receiving a first electric signal, converting the first electric signal into an ultrasound signal, transmitting the ultrasound signal towards a target, receiving the signal reflected back from the target and converting the single reflected back into a second electric signal and the transducers are unconstructed and arranged to each transmit the signal at initially a substantially diverging angle from the initial signal of the other transducer; and
measuring means for simultaneously measuring the flow of fluid flowing through a conduit on both sides of a cross-section of the conduit, responsive to the second electric signals from each transducer.

24. The probe of claim 23, wherein the transducers are flat piezoelectric plates arranged at substantially right angles to each other.

* * * * *